United States Patent [19]

Sachetto et al.

[11] Patent Number: 4,900,361

[45] Date of Patent: Feb. 13, 1990

[54] DESTRUCTURIZED STARCH ESSENTIALLY CONTAINING NO BRIDGED PHOSPHATE GROUPS AND PROCESS FOR MAKING SAME

[75] Inventors: Jean-Pierre Sachetto; Robert F. T. Stepto, both of Riehen; Heinz Zeller, Basel, all of Switzerland

[73] Assignee: Warner-Lambert Company, Morris Plains, N.J.

[21] Appl. No.: 209,151

[22] Filed: Jun. 20, 1988

[30] Foreign Application Priority Data

Jul. 7, 1987 [GB] United Kingdom ............... 8715941

[51] Int. Cl.$^4$ .................. C08L 3/00; C08L 89/00
[52] U.S. Cl. ........................... 106/213; 106/137; 106/210; 524/47; 524/52; 127/69; 127/71; 264/328.1
[58] Field of Search ............... 127/69, 71; 106/210, 106/213, 137; 264/328.1; 524/47, 52

[56] References Cited

U.S. PATENT DOCUMENTS

| | | | |
|---|---|---|---|
| 2,971,954 | 2/1961 | Kondras | 536/109 |
| 3,870,527 | 3/1975 | Kryger et al. | 106/2 |
| 4,482,386 | 11/1984 | Wittwer et al. | 106/213 |
| 4,655,840 | 4/1987 | Wittwer et al. | 106/130 |
| 4,673,438 | 6/1987 | Wittwer et al. | 106/213 |
| 4,761,186 | 8/1988 | Schara et al. | 127/71 |
| 4,790,881 | 12/1988 | Wittwer et al. | 106/213 |

Primary Examiner—Theodore Morris
Attorney, Agent, or Firm—Daniel A. Scola, Jr.; Howard Olevsky

[57] ABSTRACT

The invention refers to a process for obtaining a melt of destruction starch containing a finite amount of electrolytes comprising:

A. providing a starch material containing free electrolytes and/or bound phosphate salts,
B. removing partially or wholly the free electrolytes and/or the metallic cations from the phosphate groups of the starch,
C. optionally replacing a part or all of the free $H^+$-ions of the free phosphate groups with metallic monovalent and/or polyvalent cations,
D. conditioning the obtained starch material to a water content of 10 to 25% by weight calculated on the basis of starch and water,
E. heating said starch/water composition at elevated pressure to a temperature sufficient to essentially destructure the starch while maintaining said water content until a melt of destructurized starch is formed.

The invention further refers to the process of

F. cooling said melt (as obtained under E.) optionally after forming the melt into a shaped article, to a temperature below the glass transition temperature of said composition to form a solid shaped article.

22 Claims, No Drawings

DESTRUCTURIZED STARCH ESSENTIALLY CONTAINING NO BRIDGED PHOSPHATE GROUPS AND PROCESS FOR MAKING SAME

The present invention refers to destructurized starch containing a finite amount of electrolytes and to a process for making same.

It has recently become known that natural starch which is found in vegetable products and which contains a defined amount of water, can be treated at elevated temperature and in a closed vessel, thereby at elevated pressure, to form a melt. The process is conveniently carried out in an injection molding machine or extruder. The starch is fed through the hopper onto a rotating, reciprocating screw. The feed material moves along the screw towards the tip. During this process, its temperature is increased by means of external heaters around the outside of the barrel and by the shearing action of the screw. Starting in the feed zone and continuing in the compression zone, the particulate feed becomes gradually molten. It is then conveyed through the metering zone, where homogenization of the melt occurs, to the end of the screw. The molten material at the tip can then be further treated by injection molding or extrusion or any other known technique to treat thermoplastic melts.

This treatment, which is described in the European Pat. application No. 84 300 940.8 (Publication No. 118 240) yields a destructurized starch. The reason for this being that the starch is heated above the melting and glass transition temperatures of its components so that they undergo endothermic transitions. As a consequence a melting and disordering of the molecular structure of the starch granule takes place, so that a destructurized starch is obtained.

Although such destructurized starch is useful in molding techniques and extrusion, it has been found, that the molded parts show a relatively high incidence of surface defects and the processed materials generally have relatively low extensibilities. Further it was found, that the optimum processing temperature is in the range from about 140° C. to about 180° C.

It has now been found, that a starch which is treated according to this invention, yields a material which produces considerably less defects, has relatively higher extensibilities and can be treated at lower temperatures and lower pressures to obtain destructurization. The starch material according to the present invention also exhibits improved flow characteristics especially for the production of thin walled articles so that due to the improved processability, defective parts are minimized as well as necessary subsequent controls reduced. It is further possible to reproducibly control the temperature of melt-formation.

It is assumed, that many of the phosphate groups which are contained in certain native starches are bridged by divalent ions such as the calcium or magnesium ion. The concentration of such phosphate groups, i.e. the number of phosphate groups present per number of anhydro-glucose units (AGU), varies considerably for different starches. For potato starch this concentration is given as about one phosphate group per 200 to 400 AGU.

When such a starch is washed with a sufficient amount of water at a low pH, i.e. with dilute acid, the phosphate bridges are broken down and the free phosphate groups are produced. Many phosphate group containing starches have an "open" structure and can be easily penetrated by an aqueous medium, so that a considerable part of the divalent bridging cation can be washed out within a relatively short period of time, i.e. some minutes.

When the bridging calcium ions are washed out e.g. with dilute HCl the following reaction occurs:

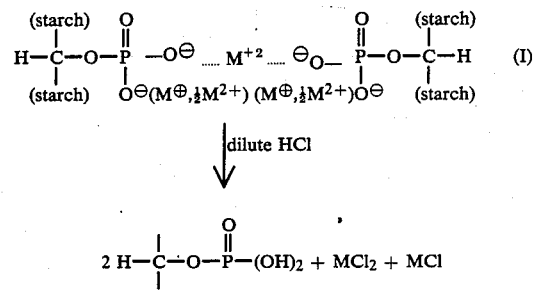

In the above formula $M^+$ means $H^+$, $Na^+$ or $K^+$; $M^{2+}$ means $Ca^{+2}$ or $Mg^{2+}$.

As can be seen, on treatment with acid, unsubstituted phosphoric acid groups are linked to the starch formed.

Herein one mole of phosphate groups corresponds to two equivalents. One mole of $M^{2+}$ corresponds to two equivalents; one mole of $M^+$ and $H^+$ to one equivalent each. One equivalent is defined as that number of moles of an ionic species which carries one mole of ionic charge.

As can be seen, from formula (I) above, a phosphate bridge contains 2 phosphate groups and a minimum of one $M^{2+}$-cation and two $M^+$ cations.

It has also been found, that starch often contains small amounts of free electrolytes, i.e. electrolytes which are not bound to phosphate groups, and which generally are water-soluble so that they can be washed out with water, preferably with demineralized water. These electrolytes may be present either originally in the potato tubers or may be introduced later during manufacturing, i.e. during processing with water and drying.

It has now been found that these free electrolytes and the types and concentrations of the cations associated with the phosphate groups influence strongly the processability of the starch in the process of destructurization and melt-formation. Especially it has been found that when the free electrolytes are being partially or wholly removed and/or when the $M^{2+}$-ions, which may bridge the phosphate groups or the metallic $M^+$-ions associated with these phosphate groups are partially or wholly removed, the processability of the starch in the process of destructurization and melt-formation is remarkably improved and the disadvantages mentioned above are overcome to a considerable extent.

The present invention refers to a process for obtaining a melt of destructurized starch containing a finite amount of electrolytes comprising:

A. providing a starch material containing free electrolytes and/or bound phosphate salts, B. removing partially or wholly the free electrolytes and/or the metallic cations from the phosphate groups of the starch, C. optionally replacing a part or all of the free $H^+$-ions of the phosphate groups with metallic monovalent and/or polyvalent cations, D. conditioning the obtained starch material to a water content of 10 - 25 % by weight calculated on the the basis of starch and water, and E. heating said starch/water composition at an elevated pressure to a temperature sufficient to essentially destructure the starch while maintaining said water content until a melt of destructurized starch is formed.

The present invention also refers to the melt of destructurized starch obtained by said process.

The present invention further refers to the process of

F. cooling said melt (as obtained under E.) optionally after forming the melt into a shaped article, to a temperature below the glass transition temperature of said composition to form a solid shaped article.

The present invention further refers to the solid article obtained by said cooling step F.

The present invention further refers to the use of such melted or destructurized starch in pressure molding techniques such as pressure molding, injection molding, blow molding or extrusion.

Optionally such destructurized starch is extruded first and cut into granules before using it in injection molding or pressure molding techniques.

Preferred is the process wherein the free electrolytes are washed out completely. It is further preferred that the metallic cations associated with the phosphate groups are removed to such an extent that the remaining number of equivalents of $Me^{2+}$ per per 100 anhydroglucose units is less than 0.3.

The term destructurized native starch has been explained above. Starch is to be understood as chemically non-modified starch. As such it includes for example also gelatinized or cooked starch and includes generally carbohydrates of natural, vegetable origin, composed mainly of amylose and/or amylopectin. It may be extracted from various plants, examples being potatoes, rice, tapioca, corn, and cereals such as rye, oats and wheat. Starches containing phosphate groups are preferably made from potato starch as well as corn starch, preferably from potato starch. Simply washing with demineralized water will completely remove the content of free electrolytes, but washing with water of low salt content may suffice. The resulting washed starch can then be processed at a lower temperature and/or at a lower pressure compared to the non-washed starch.

Neutral water, however, will remove only the free electrolytes. The processing properties of such a water-washed starch may be further improved by removing or partially removing also the metallic cations. They are eliminated by washing the starch with water of a low acid value (pH) preferably a value lower than 3 which can be obtained by adding hydrochloric acid, sulfuric acid or any other suitable inorganic or organic acid to the washing water. Preferably the so treated material is rinsed afterwards with neutral water.

Washing with acid will regularly also remove the free electrolytes, whilst washing with neutral water will leave the bound phosphate salts unchanged.

When removing cations from the phosphate groups according to step B., a value of the remaining number of $M^{2+}$ per 100 AGU of less than 0.2 is preferred and especially a value less than 0.1. Very good results were obtained with potato starch with values (after treatment) close to zero.

Once the cations are removed from the phosphate groups, the thus obtained starch will contain free —O—P(O)(OH)$_2$-groups and will become acidic. The pH can drop from about 7 to about 3.5 as measured under standard conditions in a water suspension. In some cases such a low pH may not be desirable as heating such a starch to higher temperatures may cause an undesirable degradation of the chain, resp. reduced mechanical properties of the end product.

A particular aspect of this invention is therefore concerned with the neutralization of the free acid groups, partially or wholly, resp. with the replacement of a part or of all the protons ($H^+$) of the unsubstituted phosphoric acid groups linked to the starch with other cations, which may be monovalent or polyvalent. Preferred are monovalent ions such as $Na^+$, $K^+$, $NH_4^+$ or divalent ions such as $Ca^{2+}$ or $Mg^{2+}$. These ions may be added e.g. in the form of their hydroxides.

It was found that it is possible to add divalent ions and that such ions, like calcium or magnesium, previously removed by acid washing, will not reestablish the original state of the starch, and will have a measured, positive effect on processing properties.

Whilst the elimination of free electrolytes and of the phosphate-associated metallic cations will reduce the processing temperatures and pressures, the neutralization of the free protons will increase these values at a measured rate. According to this invention it is possible to vary and to control the temperature of melt formation to optimize process conditions by adjusting the electrolyte content of the starch.

The influence of the cation content of potato starch (washed with acid and reintroduction of cations by titrating with the corresponding hydroxides) can be seen from the following Table 1.

The values for the temperature of melt-formation given in Table 1 are measured by differential scanning calorimetric analysis (DSC). This temperature of melt-formation is indicated on the DSC-diagram by a specific relatively narrow peak just prior to the endothermic change characteristic of oxidative and thermal degradation. This peak disappears as soon as the mentioned specific endothermic transition has been undergone. This last endothermic transition prior to thermal and oxidative degradation plays an important role in melt-formation, indicated by the fact that the opaque starch/water melt becomes transparent.

As is known to those skilled in the art, the melt formation behaviour, i.e. the rate of melt formation, viscosities etc. in a screw and barrel depend on many factors, such as the size of the barrel, its length and diameter, screw design, speed of rotation, heating profile, etc. It is also well-known that the nominal temperatures registered by DSC equipment are, because of the finite heat capacities of the sample and holders and the finite rates of heating used, not the temperatures of the samples. Further, the temperatures of material in the screw of an extruder or injection molding machine are, because of heats of melt-formation, structural changes and the shearing action of the screw, not the same as the set temperatures of the barrel and both of these temperatures are different from the nominal temperatures registered by the DSC equipment.

For example, the DSC analysis may show the upper transition, i.e. the point where the opaque starch/water melt become transparent, at a nominal temperature of 182° C., the temperature having been increased from 30° C. to 180° C. in 900 seconds. In spite of the lower set temperature and shorter time of the processing, e.g. in the injection molding equipment, compared with that of the DSC measurements, the upper transition will be undergone due to the real temperature in the DSC sample being lower than the nominal temperatures indicated on the DSC and additionally the set temperatures of the injection molding machine being lower than the temperatures of the material in the screw.

In Table 1 the nominal DSC-temperatures are given.

TABLE 1

Influence of the cation composition of the phosphate groups of potato starch on the melt-formation temperature of potato starch at 17% H$_2$O.

| No. | Material | Cation Composition (expressed in equivalent per 2 equivalents phosphate) | | | | Temperature of Melt Formation (°C.) (DSC) |
|---|---|---|---|---|---|---|
| | | $Ca^{++}$ | $Na^+$ | $NH_4^+$ | $H^+$ | |
| 1. | Native Starch (RX 1279) | 1 | 0.40 | — | 0.60 | 184.5 |
| 2. | Acid-Washed Starch (RX 1279) | 0 | 0 | — | 2 | 163.1 |
| 3. | $Ca^{2+}$—Starch | 2 | 0 | — | 0 | 200.5 |
| 4. | $Na^+$—Starch | 0 | 2 | — | 0 | 211.8 |
| 5. | $NH_4^+$—Starch | 0 | 0 | 2 | 0 | 199.1 |
| 6. | $Ca^{2+}$—$Na^+$—$H^+$—Starch | 1 | 0.50 | — | 0.50 | 172.6 |
| 7. | " | 1 | 0.33 | — | 0.66 | 179.1 |
| 8. | " | 1 | 0 | — | 1 | 182.3 |
| 9. | " | 0 | 1 | — | 1 | 199.3 |
| 10. | " | 0.33 | 1 | — | 0.66 | 209.6 |
| 11. | " | 1 | 1 | — | 0 | 212.3 |

From Table 1 it can be seen that the melt formation temperature of a native potato starch which is 184.5° C., can be varied over a broad range from down to 163.1° C. for a fully acid washed starch up to 212.3° C. for a starch having 1 equivalent $Na^+$ and 1 equivalent $Ca^{2+}$ per two equivalents of phosphate.

It can be seen further that re-introducing calcium in an acid-washed starch up to the level it was in the corresponding native starch, while maintaining about the same distribution of the other cations, does not bring back the melt temperature to the same level. Comparing native starch of Table 1 with a $Ca^{2+}$-$Na^+$-$H^+$ composition in equivalents respectively 1-0.40-0.60 and melt formation temperature of 184.5° C. with $Ca^{2+}$-$Na^+$-$H^+$ starch of composition 1-0.50-0.50, melt formation temperature of 172° C. and $Ca^{2+}$-$Na^+$-$H^+$ starch of composition 1-0.33-0.66 of melt formation temperature of 179.1° C., shows this clearly.

The obtained water or acid washed starch material is then conditioned to a water content in the range of about 10 to 25 % and better 10 to 20 % calculated to the weight of starch and water. Preferred is a final water content of 12 to 19 % and especially 14 to 18 % calculated to the weight of starch and water.

The conditioned starch material with the appropriate water content is then optionally mixed with further additive as described herein further below and heated at elevated pressure above its glass transition temperature and above its melting point. This temperature is preferable within the range of about 80 -200° C., preferably within the range of about 90 to 190° C., and especially at about 120° C. The minimum pressure corresponds to the water vapour pressure produced at these temperatures.

The starch material is heated preferably in a closed volume. A closed volume can be a closed vessel or the volume created by the sealing action of the unmolten feed material as happens in the screw of injection molding or extrusion equipment. In this sense the screw and the barrel of an injection molding machine or an extruder is to be understood as being a closed vessel. Pressures created in a closed vessel correspond to the vapour pressure of water at the used temperature but of course pressure may be applied as this is normally done in a screw barrel. The preferred applied pressures to be used are in the range of the pressures which are applied in extrusion process and known per se, i.e. from zero to $150 \times 10^5$ N/m$^2$ preferably from zero to $100 \times 10^5$ N/m$^2$ and most particularly from zero to $75 \times 10^5$ N/m$^2$.

The melt of destructurized starch according to this invention is e.g. injected under the normal range of injection pressures used in injection molding namely for thinner walled articles in the range from $300 \times 10^5$ N/m$^2$ to $3.000 \times 10^5$ N/m$^2$ preferably $700 \times 10^5$ -2200 $10^5$ N/m$^2$.

The starch material of the present invention may contain or may be mixed with additives such as extenders, lubricants, plasticizers and/or coloring agents.

These additives may be added before heating the starch to form the melt (step E) or after this step. It mainly depends on the intended use of the destructurized starch.

Such additives are extenders of different kinds, e.g. gelatin, vegetable proteins such as sunflower protein, soybean proteins, cotton seed proteins, peanut proteins, rape seed proteins, blood proteins, egg proteins, acrylated proteins; water-soluble polysaccharides such as: alginates, carrageenans, guar gum, agar-agar, gum arabic and related gums (gum ghatti, gum karaya, gum tragacanth) pectin; water-soluble derivatives of cellulose: alkylcelluloses hydroxyalkylcelluloses and hydroxyalkylalkylcelluloses, such as: methylcellulose, hydroxymethylcellulose, hydroxyethylcellulose, hydroxypropylcellulose, hydroxyethylmethylcellulose, hydroxpropylmethylcellulose, hydroxybutylmethylcellulose, cellulose esters and hydroxyalkylcellulose esters such as: celluloseacetylphtalate (CAP), Hydroxypropylmethylcellulose (HPMCP); carboxyalkylcelluloses, carboxyalkylalkylcelluloses, carboxyalkylcellulose esters such as: carboxymethylcellulose and their alkalimetal salts; water-soluble synthetic polymers such as: polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone, polycrotonic acids; suitable are also phtalated gelatin, gelatin succinate, crosslinked gelatin, shellac, water soluble chemical derivatives of starch, cationically modified acrylates and methacrylates possessing, for exampe, a tertiary or quaternary amino group, such as the diethylaminoethyl group, which may be quaternized if desired; and other similar polymers.

Such extenders may optionally be added in any desired amount preferably within the range of up to 50 %, preferably within the range of 3 % to 10 % based on the weight of all components.

Further additives are inorganic fillers, such as the oxides of magnesium, aluminum, silicon, titanium, etc. preferably in a concentration in the range of about 0.02 to 3 % by weight preferably 0.02 to 1 % based on the weight of all components.

Further examples of additives are plasticizers which include polyalkylene oxides, such as polyethylene glycols, polypropylene glycols, polyethylene-propylene glycols; organic plasticizers with low molecular weights, such as glycerol, glycerol monoacetate, diacetate or triacetate; propylene glycol, sorbitol, sodium diethylsulfosuccinate, triethyl citrate, tributyl citrate, etc., added in concentrations ranging from 0.5 to 15 %, preferably ranging from 0.5 to 5 % based on the weight of all the components.

Examples of coloring agents include known azo dyes, organic or inorganic pigments, or coloring agents of natural origin. Inorganic pigments are preferred, such as the oxides of iron or titanium, these oxides, known per se, being added in concentrations ranging from 0.001 to 10 %, preferably 0.5 to 3 %, based on the weight of all the components.

The sum of the plasticizer and water contents should preferably not exceed 25 %, and should most preferably not exceed 20 %, based on the weight of all the components.

There may further be added compounds to improve the flow properties of the starch material such as animal or vegetable fats, preferably in their hydrogenated form, especially those which are solid at room temperature. These fats have preferably a melting point of 50° C. or higher. Preferred are Triglycerides with $C_{12}$ -, $C_{14}$ -, $C_{16}$ -, and $C_{18}$ - fatty acids.

These fats can be added alone without adding extenders or plasticizers.

These fats can advantageously be added alone or together with mono- and/or diglycerides or phosphatides, especially lecithin. The mono- and diglycerides are preferably derived from the types of fats described above, i.e. with $C_{12}$ -, $C_{14}$ -, $C_{16}$ -, and $C_{18}$ - fatty acids.

The total amounts used of the fats mono-, diglycerides and/or lecithins are up to 5 % and preferably within the range of about 0.5 to 2 % by weight of the total composition.

It is further recommended to add silicondioxide or titaniumdioxide in a concentration of about 0.02 to 1 % by weight of the total composition. These compounds act as texturizing agent.

The materials described herein above form on heating and in a closed vessel a melt with thermoplastic properties, i.e. under controlled water-content and pressure conditions. Such a melt can be used in various techniques like thermoplastic materials. These techniques include injection molding, blow molding, extrusion and coextrusion (rod, pipe and film extrusion), compression molding, to produce known articles as produced with these techniques. These articles include bottles, sheets, films, packaging materials, pipes, rods, laminates, sacks, bags, pharmaceutical capsules.

The following examples further explain the invention.

EXAMPLE 1

Removal of soluble electrolytes by washing native potato starch with demineralized water.

10 kg of a native potato starch (sample RX 1075, Roquette) were washed in a Buechner funnel with a total of 50 liters of demineralized water. The washed starch was then pressed on the filter paper and dried in a conditioning room until it equilibrated at about 17% $H_2O$.

Analysis was carried out before and after washing and the results obtained are presented in Table 2.

TABLE 2

| | INITIAL (before washing) | FINAL (after washing) |
|---|---|---|
| No. of AGU per phosphate group | 223 | 262 |
| No. of AGU per $M^{2+}$ | 625 | 645 |
| No. of AGU per $M^+$ | 312 | 523 |

From the above results it can be seen that some free phosphate salt has been washed away from the starch. The washing water was concentrated and the dissolved salt precipitate by the addition of alcohol to the concentrate. This precipitate was filtered and purified by dissolving it again in a small volume of water and precipitating it again.

Conventional analysis of the recovered salt showed that the anion was a phosphate (strong positive test with molybdate, tests negative for carbonate, chloride, sulfate). The cations as determined by atomic absorption spectroscopy were essentially: $K^+$, $Na^+$, with minor amounts of $Ca^{2+}$ and $Mg^{2+}$.

EXAMPLE 2

Destructurization and melt-formation of washed potato starch (washing with demineralized water)

Water-washed native potato starch as obtained in example 1, a lubricant release agent (hydrogenated triglyceride), a melt flow accelerator (lecithin), and a texturizing agent ($TiO_2$) were mixed together in the relative proportions in a high speed powder mixer for 10 minutes so that a composition of 83 parts of $H_2O$-washed potato starch, 0.8 parts of the hydrogenated triglyceride containing the fatty acids $C_{18}$: $C_{16}$:$C_{14}$ in a ratio of 65:31:4 weight percent, 0.4 parts of lecithin, 0.4 parts of titanium dioxide and 17 parts of water in the form of a freely flowing powder was obtained. This powder was fed into the hopper and fed to the screw barrel having the temperature profile and the screw speed indicated in Table 3 for this trial. It was then injected into an injection molding tool for pharmaceutical containers. The important injection molding parameters were recorded and the visual quality of the molded parts (% defect level) was checked and are given also in Table 3.

TABLE 3

| Melt-formation and Injection molding parameters | UNWASHED STARCH (RX 1075, Roquette) $T_b\ T_m\ T_e\ T_n$ | WATER-WASHED STARCH (RX 1075, Roquette) $T_b\ T_m\ T_e\ T_n$ |
| --- | --- | --- |
| Temp. profile [°C.] | 90/165/165/165 | 90/165/165/165 |
| Residence Time [sec] | 690 | 690 |
| Injection Pressure [bar] | 1830 | 1500 |
| Injection Time | 0,2 | 0,2 |
| Screw Speed [rpm] | 200 | 200 |
| Back Pressure [bar] | 110 | 110 |
| Cycle Time [sec] | 9,5 | 9,5 |
| Quality | | |
| Defect Level [%] | 0,1 | 0,01 |

$T_b$ = Temperature, beginning of the screw
$T_m$ = Temperature, middle of the screw
$T_e$ = Temperature, end of the screw
$T_n$ = Temperature, nozzle It can be seen that the washed starch can be processed at a lower injection pressure and yields an improved quality level of the molded parts.

EXAMPLE 3

(Washing with dilute acid)

600 g of native potato starch were suspended in 700 ml of 0.2N HCl and stirred for 10 minutes. The suspension was filtered and the starch washed on the filter three times with 200 ml portions of 0.2N HCl. The starch was again suspended in 500 ml 0.2N HCl, stirred again for 10 minutes, filtered, washed three times with 200 ml portions of 0.2N HCl.

After this treatment with HCl the excess of acid was removed by washing with demineralized (deionized) water in following way: the starch was washed twice with 200 ml portions of deionized water and then suspended in 500 ml of deionized water. This washing procedure with deionized water (to remove excess acid) was repeated twice to get the starch free of HCl. This was controlled by adding silver nitrate to the washing water. When there was no more silver chloride precipitating in the washing water, the washing was completed. The washed starch was pressed on the filter paper and dried in a conditioning room (25° C., 40% RH) until it equilibrated at about 17.0% H₂O. In another experiment the wet starch was treated in a fluidized bed with blowing air at 50° C. until the moisture content of starch reached 17% by weight (as checked by periodical sampling of the starch).

Analyses have been carried out before and after the acid washing of starch and results obtained are given in the following Table 4:

TABLE 4

| | INITIAL (BEFORE WASHING) | FINAL (AFTER WASHING) |
| --- | --- | --- |
| No. of AGU per phosphate group | 266 | 269 |
| No. of AGU per Me$^{2+}$ | 626 | 18'000 |
| No. of AGU per M$^+$ | 617 | 20'000 |
| pH (20 g in 100 ml deionized water) | 6.8 | 3.55 |

EXAMPLE 4

(Washing with dilute acid)

3,000 g of potato starch were suspended in a mixer with 3 liters of 0.3N HCl solution and stirred with a propeller of a mixer at high speed for 5 minutes. The suspension was filtered, washed with 1 liter deionized water and put back into the mixer, suspended into 3 liters of deionized water. After stirring for 10 minutes the material was filtered again and washed on the filter with portions of deionized water until the washing water did not contain any chloride ions as shown by the silver nitrate test. The wet starch was pressed on the filter paper and then laid out on plastic trays in a conditioned room until the moisture content reached 17.2 %. The analysis is given in Table 5.

TABLE 5

| | ANALYSIS RESULTS | |
| --- | --- | --- |
| | INITIAL (BEFORE WASHING) | FINAL (AFTER WASHING) |
| No. of AGU per phosphate group | 310 | 307 |
| No. of AGU per Me$^{2+}$ | 443 | 6'400 |
| No. of AGU per M$^+$ | 690 | 25'000 |
| pH (20 g in 100 ml deionized water) | 7.5 | 4.0 |

EXAMPLE 5

Acid-washed potato starch as obtained in Example 3, a lubricant release agent (hydrogenated triglyceride) a melt flow accelerator (lecithin), a texturizing agent (TiO₂) were mixed together in the relative proportions in a high speed powder mixer for 10 minutes so that a composition of 83 parts of the starch, 0.8 parts of the hydrogenated triglyceride containing the fatty acids C$_{18}$: C$_{16}$: C$_{14}$ in a ratio of 65 : 31 : 4 weight percent, 0.4 parts of lecithin, 0.4 parts of titanium dioxide and 17 parts of water in the form of a freely flowing powder was obtained. This powder was fed into the hopper and fed to the screw barrel having the temperature profile and the screw speed indicated in Table 6 for this trial. It was then injected into an injection molding tool for tensile-test pieces. Residence time, cycle time and injection pressure are given also in Table 6.

TABLE 6

| | Temp. Profile (°C.) of the screw $T_b\ T_m\ T_e\ T_n$ | screw speed (rpm) | injection pressure (bar) | cycle time (s) | residence time (s) |
| --- | --- | --- | --- | --- | --- |
| Mixture with native starch | 90/170/170/170 | 81.6 | 1750 | 23.4 | 750 |
| Mixture of | 90/130/130/130 | 95.2 | 1300 | 7.6 | 240 |

TABLE 6-continued

| | Temp. Profile (°C.) of the screw $T_b T_m T_e T_n$ | screw speed (rpm) | injection pressure (bar) | cycle time (s) | residence time (s) |
|---|---|---|---|---|---|
| Example 5 Mixture of Example 6 Mixtures with material of Table 1 Material No. | 90/130/130/130 | 102 | 1400 | 10 | 300 |
| 3 | 90/180/180/180 | 80 | 1700 | 20 | 700 |
| 4 | 90/190/190/190 | 75 | 1720 | 20 | 720 |
| 5 | 90/180/180/180 | 80 | 1700 | 20 | 700 |
| 6 | 90/150/150/150 | 90 | 1500 | 15 | 500 |
| 7 | 90/160/160/160 | 85 | 1600 | 18 | 600 |
| 8 | 90/160/160/160 | 85 | 1600 | 18 | 600 |
| 9 | 90/170/170/170 | 82 | 1650 | 19 | 650 |
| 10 | 90/180/180/180 | 75 | 1700 | 20 | 700 |
| 11 | 90/190/190/190 | 75 | 1720 | 20 | 720 |

These results indicate that by using acid-washed starches, processing can be carried out at a lower temperature profile (40° C. below native starch). Also the cycle time and residence time were reduced which allows to increase the production rate as compared with native starch.

The results with materials No. 10 and 11 show that it is possible to process specially treated starches according to this invention at temperatures of 10 to 20° C. higher than untreated native starch. At these higher processing temperatures untreated native starch would often start to slightly decompose. The processing at higher temperature is useful in selected cases.

EXAMPLE 6

Acid-washed potato starch, as obtained in Example 4, a lubricant release agent (hydrogenated triglyceride as in Example 3) a melt flow accelerator (lecithin), a texturizing agent ($TiO_2$) were mixed together in the same relative proportions as with the acid-washed starch of Example 5, using a high speed powder mixer, for 10 minutes. The powder obtained was fed through a hopper into a screw barrel having the temperature profile and screw speed indicated in Table 6 for this trial. It was then injected into an injection molding tool for torque bar tests. Residence time, cycle time and injection pressure are also given in Table 6.

In order to compare the processing behaviour of these acid-washed starches and the quality of the injection-molded products obtained, similar mixtures were prepared using native potato starch. The corresponding powder mixture was processed with the same equipment as in the Example 5, and the temperature profile, screw torque, residence time, cycle time and injection pressure are given in Table 6.

Table 6: Comparison of the processing behaviour on an injection molding machine of mixtures containing native starches (not treated according to this invention) with the mixtures prepared from the acid-washed starches

EXAMPLE 7

100 g of acid-washed starch as obtained in Example 3 was analysed as to its content of free protons and cations. The results are given in Table 1, line 2.

This starch was then suspended in demineralized water. With an automatic titrator the respective amounts of NaOH, KOH, $NH_4OH$ and $Ca(OH)_2$ were added to obtain the other compositions shown in Table 1. As obtained when filtering and drying the obtained products, these various proportions gave a total of exchanged cations which were practically equal to the total phosphate groups of the starch. The material was then mixed with the additives as described in Example 5 and injected into a molding tool and the conditions are given in Table 6 (Materials Nos. 3 to 11).

We claim:

1. A process for obtaining a melt of destructurized starch containing a finite amount of electrolytes comprising:
   A. providing a unwashed natural starch containing free electrolytes and/or bound phosphate salts,
   B. removing partially or wholly the free electrolytes and/or the metallic cations from the phosphate groups of the starch,
   C. optionally replacing a part or all of the free $H^+$-ions of the phosphate groups with metallic monovalent and/or polyvalent cations,
   D. conditioning the obtained starch material to a water content of 10–25% by weight calculated on the basis of starch and water, and
   E. heating said starch/water composition at an elevated pressure to a temperature sufficient to essentially destructure the starch while maintaining said water content until a melt of destructurized starch is formed.

2. A process according to claim 1, wherein only the free electrolytes are being washed out.

3. A process according to claim 1, wherein the free electrolytes and the metallic cations of the bound phosphate groups are washed out.

4. A process according to claim 3, wherein in step B. the cations from the phosphate groups of the starch are removed to such an extent that the remaining number of equivalents of $M^{2+}$ per 100 anhydro-glucose units is less than 0.3.

5. The process according to claim 4, wherein when removing the cations from the phosphate groups of the starch according to step B., a value of the remaining number of $M^{2+}$ per AGU of less than 0.2 and especially a value less than 0.1 and preferably a value close to zero is obtained.

6. A process according to anyone of the claims 1 to 5, wherein in step C. a part or all of the free $H^+$-ions of the unsubstituted phosphoric acid groups linked to the starch are being replaced partly or wholly by at least one metallic monovalent or divalent ion, preferably selected from $Na^+$, $K^+$, $NH_4^+$, $Ca^{2+}$ and $Mg^{2+}$.

7. A process according to claim 1, wherein the starch is selected from potato starch or corn starch, and preferably is potato starch.

8. A process according to claim 7, wherein the destructurized starch material is conditioned to a water content in the range of about 10 to 25% and better 10 to 20% calculated to the weight of starch and water, preferably to a final water content of 12 to 19% and especially 14 to 18% calculated to the weight of starch and water.

9. A process according to claim 8, wherein said starch contains or is mixed with extenders, lubricants, plasticizers, and/or coloring agents, wherein these additives have been added before heating the starch to form the melt (step E.) or after this step.

10. A process according to claim 9, wherein the solid destructurized starch/water material is heated to a temperature within the range of about 80 to 200° C., preferably within the range of about 90 to 190° C.

11. A process according to claim 9, wherein the destructurized starch/water material contains or is mixed with at least one member selected from the class consisting of extenders, preferably with gelatin; vegetable proteins preferably sunflower protein, soybean proteins, cotton seed proteins, peanut proteins, rape seed proteins, blood proteins, egg proteins, acrylated proteins; water-soluble polysaccharides, preferably alginates, carrageenans, guar gum, agar-agar, gum arabic, gum ghatti, gum karaya, gum tragacanth, pectin; water-soluble derivatives of cellulose, preferably alkylcelluloses, hydroxyalkylcelluloses, hydroxyalkylalkylcelluloses, cellulose esters and hydroxyalkylcellulose esters, carboxyalkylcelluloses, carboxyalkylcellulose esters, polyacrylic acids and polyacrylic acid esters, polymethacrylic acids and polyacrylic acid esters, polyvinylacetates, polyvinylalcohols, polyvinylacetatephtalates (PVAP), polyvinylpyrrolidone, polycrotonic acids; phtalated gelatin, gelatin succinate, crosslinked gelatin, shellac, water soluble chemical derivatives of starch, cationically modified acrylates and/or methacrylates possessing in an amount up to and including 50 %, preferably within the range of 3 % to 10 % based on the weight of all components.

12. A process according to claim 1 or 9, wherein the destructurized starch/water material contains or is mixed with at least one member selected from the group consisting of plasticizers, including polyalkylene oxides, preferably polyethylene glycols, polypropylene glycols, polyethylene-propylene glycols; glycerol, glycerol monoacetate, diacetate or triacetate; propylene glycol, sorbitol, sodium diethylsulfosuccinate, triethyl citrate, tributyl citrate (added in concentrations ranging from 0.5 to 15 %, preferably ranging from 0.5 to 5 % based on the weight of all the components).

13. A process according to claim 1 or 9, wherein the destructurized starch contains or is mixed with at least one coloring agent selected from a member of the group of azo dyes, organic or inorganic pigments, or coloring agents of natural origin, preferably from oxides of iron or titanium, said coloring agent being added in concentrations ranging from 0.001 to 10%, preferably 0.5 to 3%, based on the weight of all components.

14. A process according to claim 1 or 11 to 13, wherein the destructurized starch/water material contains or is mixed with inorganic fillers, preferably the oxides of magnesium, aluminum, silicon or titanium, preferably in a concentration in the range of about 0.02 to 3% by weight, preferably 0.02 to 1% based on the weight of all components.

15. A process according to claim 12, wherein a plasticizer is present and the sum of the plasticizer and water content does not exceed 25%, and preferably not exceeds 20%, based on the weight of all the components.

16. A process according to claim 1, wherein the destructurized starch/water material comprises or is mixed with a material comprising animal or vegetable fats, preferably in their hydrogenated form, especially those which are solid at room temperature.

17. A process according to claim 16, wherein the destructurized starch/water material comprises or is mixed with a material comprising fat together with at least one member selected from the group of monoand-/or diglycerides or phosphatides, especially lecithin, whereby the total amounts used of the fats mono-diglycerides and/or lecithins not greater than 5% and preferably within the range of about 0.5 to 2% by weight of the total composition.

18. The melt of destructurized starch as obtained by the process according to claims 1, 5, 10 or 11.

19. The process according to claim 1 further comprising the step of:
F. cooling the melt obtained under step E subsequent to forming the melt into a shaped article, to a temperature below the glass transition temperature of said composition to form a solid shaped article.

20. The process according to claim 1 further comprising the step of:
subjecting the resultant melt of step E to a pressure molding process selected from the group consisting of injection molding, extrusion, coextrusion, compression molding and combinations thereof to form a shaped article.

21. A solid article according to claim 20, in the form of bottles, sheets, films, packaging materials, pipes, rods, laminates, sacks, bags, granulates or pharmaceutical capsules.

22. A starch containing a finite amount of electrolytes as obtained by a process comprising:
A. providing a unwashed natural starch containing free electrolytes and/or bound phosphate salts,
B. removing partially or wholly the free electrolytes and/or the metallic cations from the phosphate groups of the starch,
C. optionally replacing a part or all of the free $H^+$-ions of the free phosphate groups with metallic monovalent and/or polyvalent cations, and
D. conditioning the obtained starch material to a water content of 10 –25% by weight calculated on the basis of starch and water.

* * * * *